United States Patent
Honkura et al.

(10) Patent No.: US 6,932,607 B2
(45) Date of Patent: Aug. 23, 2005

(54) KEEPER FOR A DENTAL MAGNETIC ATTACHMENT

(75) Inventors: Yoshinobu Honkura, Tokai (JP); Kazuo Arai, Tokai (JP); Aki Watarai, Tokai (JP); Yasuhiro Takeuchi, Tokai (JP)

(73) Assignee: Aichi Steel Corporation, Tokai (JP)

( * ) Notice: Subject to any disclaimer, the term of this patent is extended or adjusted under 35 U.S.C. 154(b) by 114 days.

(21) Appl. No.: 10/394,226

(22) Filed: Mar. 24, 2003

(65) Prior Publication Data

US 2004/0063072 A1 Apr. 1, 2004

(30) Foreign Application Priority Data

Sep. 26, 2002 (JP) .................................. 2002-281636

(51) Int. Cl.$^7$ .............................................. A61C 13/235
(52) U.S. Cl. ................................................... 433/189
(58) Field of Search ................................ 433/173, 172, 433/174, 175, 176, 189, 221, 220

(56) References Cited

U.S. PATENT DOCUMENTS

| | | |
|---|---|---|
| 4,431,419 A | 2/1984 | Portnoy |
| 4,824,371 A * | 4/1989 | Deutsch et al. ............. 433/189 |
| 6,302,694 B1 * | 10/2001 | Honkura et al. ............ 433/189 |
| 2002/0137010 A1 * | 9/2002 | Honkura et al. ............ 433/189 |

FOREIGN PATENT DOCUMENTS

| | | |
|---|---|---|
| EP | 1 099 419 | 5/2001 |
| FR | 2 587 895 | 4/1987 |

* cited by examiner

*Primary Examiner*—Cary E. O'Connor
(74) *Attorney, Agent, or Firm*—Oblon, Spivak, McClelland, Maier & Neustadt, P.C.

(57) ABSTRACT

The aim of the present invention is to offer a keeper for a dental magnetic attachment that is strong, has low manufacturing costs, and is not easily detached from the tooth root. The keeper proposed herein has a keeper body, which is shaped like a plate, and a root, which is attached to the bottom of the keeper body. The keeper body and the root are machined from a single piece of soft magnetic material in one piece. The root has a smaller diameter part that is linked to a larger diameter part whose external diameter is larger than an external diameter of the smaller diameter part. The smaller diameter part is linked to the bottom of the keeper. There are multiple circumferential grooves around the outer side of the larger diameter part.

4 Claims, 3 Drawing Sheets

KEEPER FOR A DENTAL MAGNETIC ATTACHMENT

CROSS-REFERENCES TO RELATED APPLICATIONS

The present application claims priority under 35 U.S.C. §119 to Japanese Patent Application No. 2002-281636, filed Sep. 26, 2002, entitled "A KEEPER FOR A DENTAL MAGNETIC ATTACHMENT". The contents of this application are incorporated herein by reference in their entirety.

BACKGROUND OF THE INVENTION

1. Field of the Invention

The present invention relates to a keeper of a dental magnetic attachment that fixes a denture by using magnetic attractive force.

2. Discussion of the Background

A dental magnetic attachment that fixes a denture by using magnetic attractive force has already been developed in the dental field. The prior dental magnetic attachment 9, as shown in FIG. 3, comprises a magnetic assembly 91 embedded in a denture 81 and a keeper 92 embedded in a root cap 82 to contact the magnetic assembly 91. The keeper 92 is made of soft magnetic material that generates attractive force between the keeper 92 and the magnetic assembly 91.

The dental magnetic attachment in this structure requires the condition that the keeper 92 is cast in the root cap 82. The casting process in which the keeper 92 is incorporated into the root cap 82 requires precise control of casting conditions at an elevated temperature to maintain the good quality of the keeper 92. The process requires a lot of time and is prone to various problems. As the result, the cost of keeper preparation is increased significantly. It also prolongs the medical treatment period for the patient.

Therefore, recently, a keeper is cemented directly on the tooth root surface using advanced dental resin that has been developed. This type of keeper 92, as is shown in FIG. 4, comprises a keeper body 921 and a root 922 which are linked together by welding. (cf. Unexamined patent application publication 2000-137260)

However, the keeper 92 mentioned above faces the following difficulties.

As mentioned above, in the keeper 92, the keeper body 921 and the root 922 are connected by welding. The root 922 is sometimes referred to as a post. Therefore the welding process, which takes a lot of time and labor, makes it difficult to decrease the cost of the keeper. The welded structure itself has no special problem in strength, but because of the nature of welding, it is not possible to overcompensate very much on weld strength so there is not much leeway when it comes to strength. So the strength of the border between the keeper body and the root part, that is, the strength of the keeper has been required to be elevated.

The prior keeper 92, as is shown in FIG. 4, has an excellent structure that has a smaller diameter bendable part 923 and that enables the root 922 to be bendable. Moreover, a step part between the bendable part 923 and larger diameter taper part 924 prevents embedded keeper 92 from coming off.

But the step part is not enough to prevent the keeper 92 from coming off and more excellent structure to prevent coming off has been required.

SUMMARY OF THE INVENTION

Considering these difficulties, the present invention provides a keeper for the dental magnetic attachment that is low in manufacturing cost, and is superior in prevention of coming off and strength.

The present invention is directed to a keeper of dental magnetic attachment so as to be attracted by a magnetic assembly embedded in a denture base.

This keeper includes a keeper body which is shaped like a plate and a root positioned on the bottom of the keeper body. The keeper body and the root are made of the same soft magnetic material and are machined from a single piece of soft magnetic material to make the keeper in one piece.

In the root, a smaller diameter part is linked to a larger diameter part whose external diameter is larger than an external diameter of the smaller diameter part, and the smaller diameter part is also linked to the bottom of the keeper body.

The outer side of the larger diameter part has multiple circumferential grooves that are made circumferentially.

In this keeper, as is mentioned above, the keeper body and the root positioned on the bottom of the keeper body machined from one piece of soft magnetic material. Therefore the process of welding a root to a keeper body can be omitted. As a result of this, elevated strength and the lower manufacturing cost are realized.

The root comprises the smaller diameter part and the larger diameter part, and there is inevitably a step part between them. Furthermore on the outer side of the larger diameter part there are the multiple circumferential grooves. So, in this keeper, dental resin used to be embedded between the keeper and tooth root gets strongly meshed together with the step part and the circumferential grooves. Therefore this keeper can be anchored more strongly thus elevating the prevention of coming off.

Accordingly the present invention provides a keeper of dental magnetic attachment that is low in manufacturing cost, high in prevention of coming off, and high in strength.

BRIEF DESCRIPTIOPN OF THE DRAWINGS

A more complete appreciation of the invention and many of the attendant advantages thereof will become readily apparent with reference to the following detailed description, particularly when considered in conjunction with the companying drawings, in which.

DESCRIPTION OF THE PREFERD EMBODIMENTS

Figure 1:
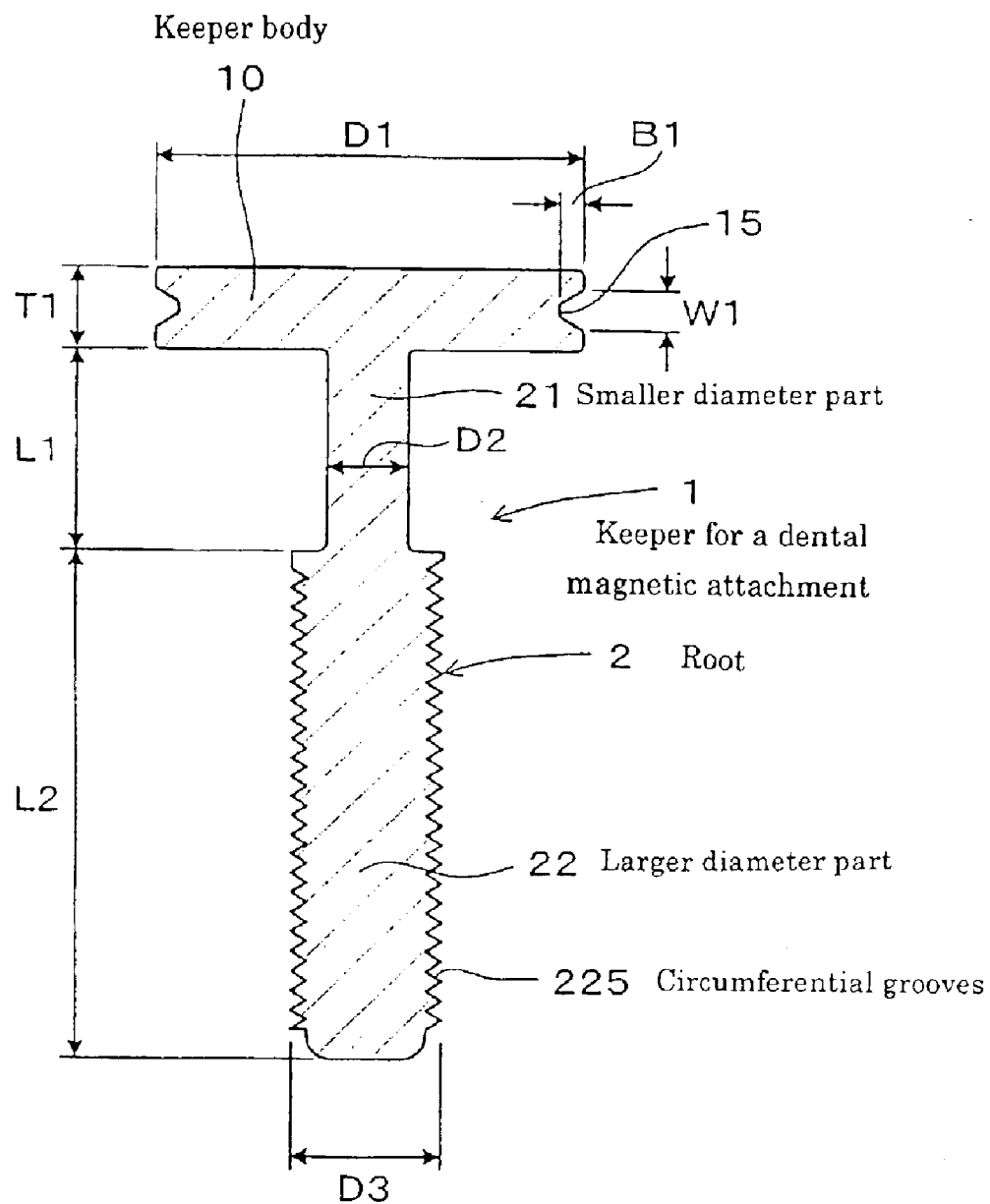
FIG. 1 is a perspective view of a keeper of the first embodiment.

In this invention, as mentioned above, the root consists of a smaller diameter part and a larger diameter part. Controlling proper strength of the smaller diameter part enables the smaller diameter to be bent. In this case, it is easy to change the angle between a root and a keeper body to a desired angle. For example, in the case that a tooth root is tilted and its canal is also tilted, the root can be adjusted to the angle of the canal by bending the smaller diameter part of the root. Therefore the present keeper can be adaptable to any shape of a tooth root.

It is preferable that the circumferential grooves made on the larger diameter part of the root take the form of a screw thread that winds spirally. That is to say, it is preferred to make the larger diameter part itself male screw like. In this case, more circumferential grooves can be made enabling improvement of anchoring. Additionally, in the case that it is necessary to take the keeper off the tooth root, it can be taken out little by little by rotating the whole keeper along the screw thread. Therefore in case it is necessary to take a keeper out of the oral cavity, it is possible to take out the whole keeper easily.

It is preferable that a body groove is made circumferentially on the outer side of the keeper body.

In this case, dental resin that is embedded between the keeper body and the tooth root meshes together with the body groove and yields anchoring effect, thus elevating the prevention of coming off of the keeper.

Also, it is preferred that the outer side of the keeper body have at least two places that are flat and that are parallel to the axial direction so as to be able to be grasped by a tool. In this case, by fitting a tool to the places, rotating or other action can be done accurately.

It is preferred that the axial length of the smaller diameter part is longer than twice the external diameter of the smaller diameter part. This makes it easy to get a smooth bent condition when the smaller diameter is bent. On the other hand, in the case that the axial length of the smaller diameter part is less than twice its external diameter, stress is concentrated to both ends of the smaller diameter part and it makes it difficult to get smooth bent condition. As a result, there is the danger of insufficient strength. Therefore the axial length of the smaller diameter part is preferred to be at least 2.5 times greater than the external diameter of the smaller diameter part. It is best that the length be at least 3 times the diameter. The limit of the length of the smaller diameter part is naturally decided by the proper length of the root.

The external diameter of the smaller diameter part is preferred to be 0.6–1.2 mm. In the case that the external diameter of the smaller diameter part is shorter than 0.6 mm, the strength is too weak and durability of the keeper may be reduced. On the other hand, in the case that the external diameter of the smaller diameter part is above 1.2 mm, it is difficult to bend the smaller diameter part.

The external diameter of the larger diameter part is preferred to be larger than the external diameter of the smaller diameter part by 0.2 mm or more. In the case that the external diameter difference between the smaller diameter part and the larger diameter part is less than 0.2 mm, the anchoring effect by the step part between them is insufficient. The external diameter of the larger diameter part is limited by the size of the canal made in the tooth root, and is usually 2 mm or less.

Also, the larger diameter part can have a taper part that gets smaller towards the tip. In this case, the root is more smoothly inserted into the canal in the tooth root.

Preferred Embodiments

First Embodiment

The embodiments of the keeper for the dental magnetic attachment according to the present invention will be described with reference to FIG. 1 and FIG. 2

Figure 3:
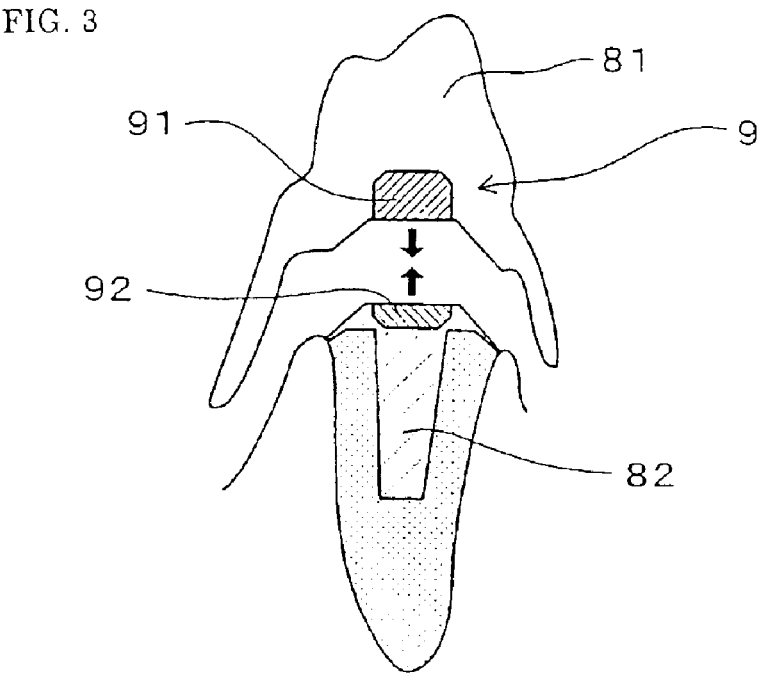
FIG. 3 is an illustration of the structure of the dental magnetic attachment of a prior art.
Figure 4:
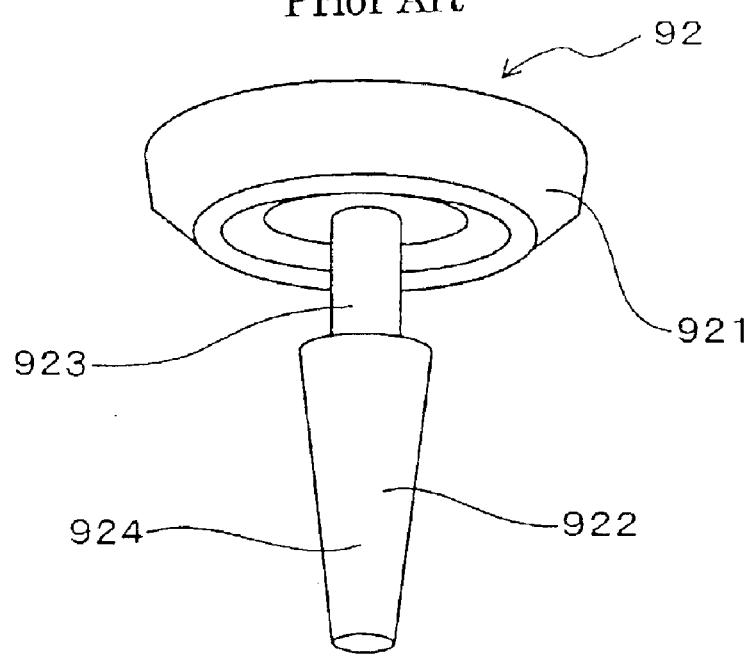
FIG. 4 is a perspective view of a keeper of a prior art.

The keeper 1, as shown in FIG. 3, is the keeper for the dental magnetic attachment that is attracted by the magnetic assembly 91 embedded in denture 81.

The keeper 1 of this example comprises the keeper body 10 that is shaped like a plate and the root 2 positioned on the bottom of the keeper body 10. The keeper body 10 and the root 2 are machined from the same piece of soft magnetic material.

In the root 2, a smaller diameter part 21 is linked with the larger diameter part 22 whose external diameter is larger than an external diameter of the smaller diameter part 21, and the smaller diameter part 21 is also linked to the bottom of the keeper body 10. The outer side of the larger diameter part 22 has multiple circumferential grooves 225.

Thereinafter the details will be described.

The keeper 1 is machined from a single piece of soft magnetic material, Fe-19Cr-2Mo-0.2Ti soft magnetic stainless steel. By this machining process, as shown in FIG. 1, disc-like keeper body 10 and root 2, which has a smaller diameter part 21 and a larger diameter part 22, are formed as one body by machining.

In this example, as shown in the same figure, circumferential grooves 225 take the form of a screw thread wound spirally on the larger diameter part 22 of the root 2.

Furthermore, the outer side of the keeper body 10 has a body groove 15 made by circumferential machining.

As for specific dimensions, an external diameter D1 of the keeper body 10 is $\phi$4.0 mm and a thickness T1 is 0.8 mm. A width W1 of the body groove 15 is 0.4 mm, and a depth B1 is 0.2 mm. A length L1 of the smaller diameter part 21 is 2.0 mm and an external diameter D2 is $\phi$0.75 mm. A length L2 of the larger diameter part 22 is 5.0 mm and an external diameter D3 is $\phi$1.4 mm.

Next, the embodiment of the installation structure of the present keeper 1 will be described with reference to FIG. 2.

Figure 2:
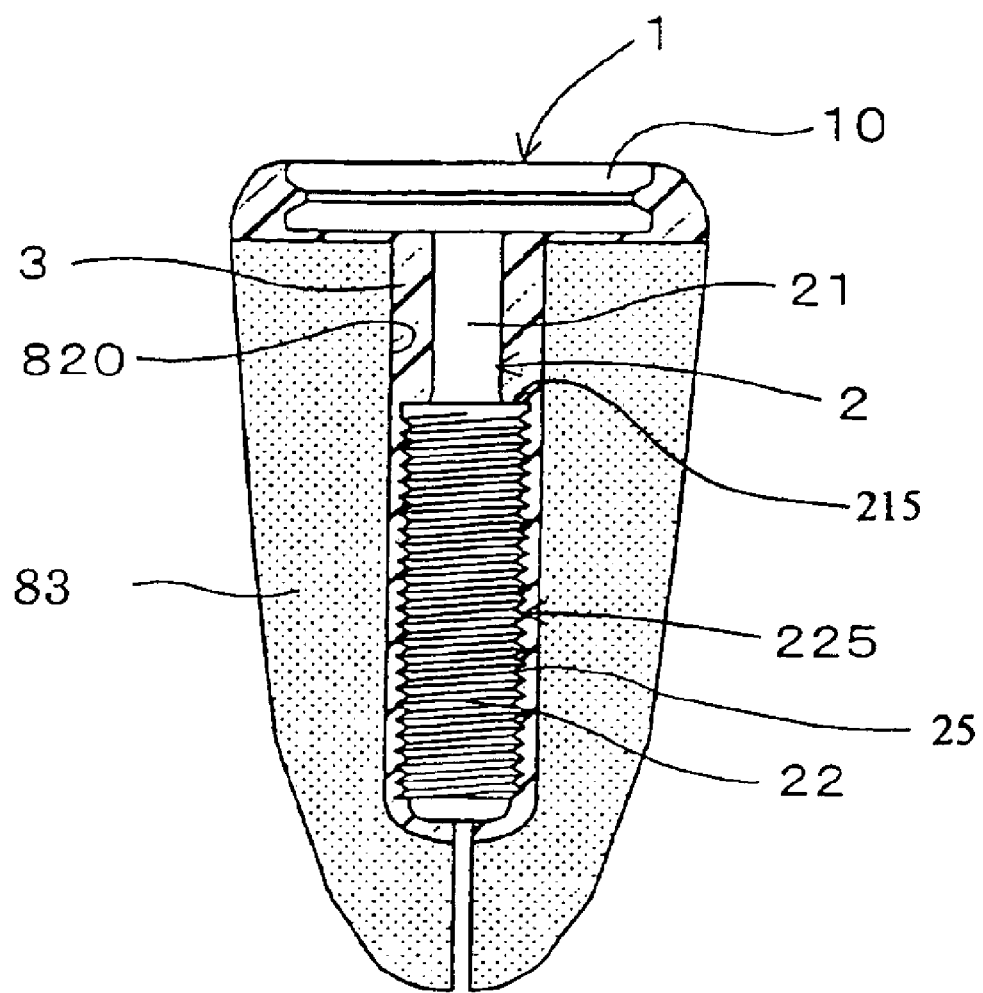
FIG. 2 is an illustration of an installation of the keeper of the first embodiment.

The structure shown in FIG. 2 is an example wherein the tooth root 83 is almost vertical and the keeper 1 is embedded in the vertical canal 820. In this case as shown in FIG. 2, the keeper is used in a condition that the keeper body 10 is kept vertical to the root 2 without bending. The root 2 is inserted into the root canal 820 of the tooth root 83, and the keeper 1 is firmly embedded in the tooth root 83 with the dental resin 3 around the root 2 and the keeper body 10. In the case that tooth root 83 is at an incline and root canal 820 is made at an incline, root 2 is tilted with respect to the keeper body 10 by bending the smaller diameter part 21 of root 2 according to the incline of root canal 820 (not shown in the figure). Therefore, even if tooth root 83 is at an incline, the keeper body 10 is easily embedded in the horizontal condition.

In the following the effects of present invention are described.

The keeper 1 for the dental magnetic attachment has a keeper body 10 and root 2 that are both made of a single soft magnetic material by machining in one piece. Therefore the cost of the manufacturing process, in comparison with the prior process of welding a root on a keeper body, is reduced.

The present root 2 has a bendable smaller diameter part 21. Therefore the angle of the root 2 to the keeper body 10 can be easily changed to a desirable condition. So such has an excellent adaptability to a various shapes of a tooth root.

The root 2 has a step part 215 between the smaller diameter part 21 and the larger diameter part 22. Furthermore the outer side of the larger diameter part 22 has multiple circumferential grooves 25, which take the form of a spiral screw thread.

Also the outer side of the keeper body has, as mentioned above, the body groove 15.

Therefore when the step part 215, multiple circumferential grooves 25 and groove 15 are firmly embedded in tooth root 83 with dental resin between the tooth root 83 and the keeper 1, the keeper 1 is extremely strongly anchored.

As mentioned above, circumferential grooves 25 of the larger diameter part 22 take the form of a spirally wound screw thread. If it is necessary to remove the keeper 1 from the tooth root 83, the keeper 1 can be removed from the tooth root by rotating keeper 1 about the axis of root 2, like loosening a screw. This enables the keeper 1 to be removed relatively easily.

Obviously, numerous modifications and variations of the present invention are possible in light of the above teachings. It is therefore to be understood that, within the scope of the appended claims, the invention may be practiced otherwise than as specifically described here.

What is claimed is:

1. A keeper for a dental magnetic attachment to be attracted by a magnetic assembly embedded in a denture base, the keeper comprising:
   a keeper body which is shaped like a plate, and
   a root that is positioned on the bottom of the keeper body,
   wherein the keeper body and the root are made of a same soft magnetic material and are machined from a single piece of the soft magnetic material in one piece,
   wherein the root has a smaller diameter part that is linked to a larger diameter part whose external diameter is larger than an external diameter of the smaller diameter part,
   wherein the smaller diameter part is linked to the bottom of the keeper body,
   wherein the outer side of the larger diameter part has multiple circumferential grooves that are made circumferentially,
   wherein the circumferential grooves that are made on the larger diameter part of the root take the form of a screw thread, and
   wherein the outer side of the keeper body has a body groove that is made circumferentially.

2. A keeper for a dental magnetic attachment according to claim 1, wherein an axial length of the smaller diameter part is longer than twice an external diameter of the smaller diameter part.

3. A keeper for a dental magnetic attachment according to claim 1, wherein an external diameter of the smaller diameter part is from 0.6 mm to 1.2 mm.

4. A keeper for a dental magnetic attachment according to claim 1, wherein an external diameter of the larger diameter part is larger than an external diameter of the smaller diameter part by 0.2 mm or more.

* * * * *